(12) United States Patent
Ko et al.

(10) Patent No.: US 6,619,747 B2
(45) Date of Patent: Sep. 16, 2003

(54) TORSO AND FOREARM SUPPORTING DEVICE FOR CHAIRS AND WORKSTANDS

(75) Inventors: Kam Ko, 92 Morrison Crescent, Unionville, Ontario (CA), L3R 9K8; Kay K. Lau, Eilat (IL)

(73) Assignee: Kam Ko (CA)

( * ) Notice: Subject to any disclaimer, the term of this patent is extended or adjusted under 35 U.S.C. 154(b) by 4 days.

(21) Appl. No.: 09/842,348

(22) Filed: Apr. 25, 2001

(65) Prior Publication Data

US 2002/0158492 A1 Oct. 31, 2002

(51) Int. Cl.[7] ................................................. A47C 7/50
(52) U.S. Cl. ............................. 297/423.12; 297/411.31; 297/411.35; 297/411.37; 248/118.3; 248/118.5
(58) Field of Search ........................ 297/353, 411.25, 297/411.35, 411.37, 115, 116, 117, 161, 118, 195.11, 215.13, 423.11, 423.12, 311, 316, 411.32, 411.33, 340, 338, 337, 411.38, 410, 411.31; 248/282.1, 285.1, 284.1, 286.1, 118.3, 118.5

(56) References Cited

U.S. PATENT DOCUMENTS

| | | | |
|---|---|---|---|
| 3,754,787 A | 8/1973 | Garber | 297/390 |
| 4,277,102 A | 7/1981 | Aaras et al. | 297/411 |
| 4,607,882 A | 8/1986 | Opsvik | 297/195 |
| 4,650,249 A | 3/1987 | Serber | 297/313 |
| 4,687,167 A * | 8/1987 | Skalka et al. | 248/282 |
| 4,832,407 A | 5/1989 | Serber | 297/437 |
| 4,943,117 A | 7/1990 | Brown | 297/392 |
| 5,171,317 A | 12/1992 | Corcoran | 606/241 |
| 5,281,001 A | 1/1994 | Bergsten et al. | 297/411.24 |
| 5,295,728 A | 3/1994 | Schaevitz | 297/195.1 |
| 5,369,805 A | 12/1994 | Bergsten et al. | 297/411.35 |
| 5,380,065 A * | 1/1995 | Rohrer | 297/411.37 |
| 5,401,078 A | 3/1995 | Riach | 297/423.11 |
| 5,487,590 A | 1/1996 | Haynes | 297/344.14 |
| D369,691 S | 5/1996 | Haynes | D6/367 |
| D370,569 S | 6/1996 | Opsvik | D6/360 |
| 5,542,746 A | 8/1996 | Bujaryn | 297/423.12 |
| 5,597,207 A | 1/1997 | Bergsten et al. | 297/411.35 |
| 5,651,586 A | 7/1997 | Groth | 297/411.37 |
| 5,655,814 A * | 8/1997 | Gibbs | 297/411.38 |
| 5,752,683 A * | 5/1998 | Novis et al. | 248/118 |
| 5,762,402 A | 6/1998 | Gillotti | 297/423.11 |
| 5,772,174 A * | 6/1998 | Hirsch et al. | 248/447.1 |
| 5,851,054 A | 12/1998 | Bergsten et al. | 297/411.35 |
| 5,908,221 A * | 6/1999 | Neil | 297/411.36 |
| 5,971,485 A | 10/1999 | Clark | 297/423.12 |
| 5,975,640 A * | 11/1999 | Chen | 297/411.37 |
| 6,022,079 A | 2/2000 | Bergsten et al. | 297/411.35 |
| 6,042,064 A * | 3/2000 | Hong | 248/118.5 |
| 6,065,808 A | 5/2000 | Tinsley | 297/432.11 |
| 6,086,156 A * | 7/2000 | Breen et al. | 297/411.37 |
| 6,193,315 B1 * | 2/2001 | Hoshino | 297/353 |
| 6,213,556 B1 * | 4/2001 | Chen | 297/411.35 |
| 6,347,771 B1 * | 2/2002 | Lauzon et al. | 248/118 |

* cited by examiner

Primary Examiner—Peter M. Cuomo
Assistant Examiner—Stephen Vu
(74) Attorney, Agent, or Firm—Mark Kusner; Michael A. Jaffe

(57) ABSTRACT

A torso and forearm support is provided for supporting the body of a user resting in a seated or standing position with forearm supports for allowing the user to rest at least one forearm during forearm movement while continuously engaging the armrest. The forearm supports are individually adjustable vertically and rotatably to accommodate the dynamic and/or continuous movement of the user's arm(s). Articulated armrest brackets fold in a compact manner behind the post assembly for storage when not in use.

12 Claims, 17 Drawing Sheets

TORSO AND FOREARM SUPPORTING DEVICE FOR CHAIRS AND WORKSTANDS

TECHNICAL FIELD

The invention relates to a torso and forearm supporting device, such as in one embodiment, a swivel chair mounted on a roller base for use in a chest-supported straddle posture, having the capability of being used in a back-supported posture as well, with cushioned chest support and articulated forearm supports that follow the user's arm movement while providing continuous forearm support.

BACKGROUND OF THE ART

In order to suit the body positions required during work by industrial or commercial workers, surgeons or dentists, various ergonomic, multi-position work stands and chairs have been developed.

In industrial or commercial applications, workers are often required to remain seated or standing in one position for extended periods of time. For example, during welding operations, in an assembly environment, in a food processing operation, during clerical work such as typing or mail sorting, or during surgical or dental operations, the arrangement and configuration of seating or standing positions varies considerably. Flexibility and ease of positioning equipment is highly desirable to suit the individual needs of a person, their particular preferences in position or a variety of positions and to suit the industrial or commercial operations in which they are engaged.

In the past, clerical or industrial workers were expected to stand or sit in fixed and/or suspended positions with very little consideration of their comfort or physical well-being. In recent years, however, ergonomic seating, accident prevention and prevention of fatigue have become very prominent concerns for workers and employers alike. Many medical conditions are caused by extended physical strain usually resulting from a fixated or suspended body position or repetitious movement during work activities. For example, in keyboard-related work, the carpal tunnel syndrome has become a well-known condition caused by the compression of the nerves that pass through the wrist into the hand and is characterised by weakness, pain and disturbances in the nerves of the hand. Many proposed solutions to this syndrome have been made in the prior art geared generally to resting the forearm or wrists of a typist on a stationary wrist or forearm support in a particular position.

Examples of clerical-type supports are found in U.S. Pat. No. 4,650,249 to Serber that shows an ergonomic seating assembly including knee support pads and a wrist support platform. U.S. Pat. No. 4,832,405 to Serber also shows a variable posture chair wherein the user may take a back-supported seating position in a traditional manner and may also support their chest by taking a chest-supported straddle position sitting with elbows or forearms resting on lateral armrest extensions of the seat back.

Some of the prior art systems are very complex, with multiple components that require cumbersome adjustments. In such cases, the advantages of wrist and chest support do not overcome the disadvantages caused by interference to normal body movement due to the mechanical complexity of the device. One example is shown in U.S. Pat. No. 5,542,746 to Bujaryn which includes knee supports, chest supports, adjustable arm and wrist supports that many users would find baffling and that would unduly interfere with normal activities.

It has been recognized in the prior art that surgeons, dentists and industrial workers can also benefit from improved physical support during their work since they must remain in a fixed position, leaning over a patient for example, for extended periods of time. For example, U.S. Pat. No. 3,754,787 to Garber provides a saddle-type seat with a chest support to enable surgeons in an operating room environment to remain in a standing or sitting position leaning over a patient for extended periods of time. The surgeon's hands and arms are completely suspended while they lean over the patient, with their chest supported on a cushioned pad. Standing for extended periods of time without chest support in this type of position becomes extremely uncomfortable and stressful.

A further example of non-clerical body supports is shown in U.S. Pat. No. 5,295,728 to Schaevitz which shows a multi-position work stand with a bicycle type adjustable seat and back rest that can be used in various positions to support workers during industrial activities.

A significant disadvantage of many of the prior art devices is that while they are suitable for certain specialised uses, they are not generally suitable for both general office seating and specialised positions. An example of this disadvantage can be seen in a dental office environment. Quite often the practitioner uses the same conventional swivel chair to perform office type work at a desk as well as to carry out typical dental examinations. In such situations a conventional office swivel chair may be all that is required. However, the dentist is also often required to stand and lean over a patient for extended periods of time. A specialised work stand is simply impractical since the dentist's working environment is typically congested, and space for additional equipment is very limited.

The same disadvantages can be found in many industrial applications such as soldering, welding, assembly of electronic or mechanical components, or in chemical laboratories where workers are often seated at a desk, counter or workstation table on a conventional swivel-type chair. Workers are often required to maintain their arms in positions that result in fatigue and undue stress over extended periods of time. For example, during electrical assembly, soldering or welding, workers may be required to lean their elbows on the work piece or on a worktable to maintain their forearms in a fixed position. The costs and space requirements necessary to install specialised arm supports or work stands to support the workers in a chosen position are simply too impractical and not cost-justified. Even if specialised work stands were provided, many workers would simply reject them if they were overly complex and required adjustments that interfered with normal work patterns.

A distinct disadvantage of many prior art armrest supports is that the armrests remain stationary. As a result, the user must slide their forearms repeatedly over the arm rests and potentially suffer friction burns or abrasion. For example, U.S. Pat. No. 4,277,102 to Aaras et al. provides armrests that can be adjusted to any fixed position or orientation. However, sliding on the fixed supports will eventually result in abrasion or discomfort, if the user must move their arms often during work operations.

Recognizing this problem, U.S. Pat. No. 5,281,001 to Bergsten et al. provides a sliding and rotating arm support that enables the user to retain their forearm or elbow in the arm rest support and track the motion with a smooth linear ball slide arrangement. The Bergsten device does not include rotational adjustment and therefore can operate in a generally horizontal plane only. In addition, the Bergsten device includes a horizontally sliding arm disposed on an armrest at kidney or underarm height that likely interferes with the use of the chair or work area by unexpectedly prodding, slapping or poking the inattentive user.

Therefore, it is an object of the invention to provide an arm support that dynamically follows and simulates natural arm movement with minimal disruption to the natural arm motion of the user and with minimal cumbersome manoeuvring of an apparatus.

A further object of the invention is to provide a simple effective means to fully support any individual who is required to sit or stand in a fixated position with suspended forearms for prolonged periods. It is a further object of the invention to provide a torso and forearm supporting chair with chest support that is equipped with forearm supports and can alternatively be used in a conventional back-supported seating position with arm supports used in a conventional lateral position or alternatively retracted so that they do not interfere with normal working actions.

It is a further object of the invention to provide arm supports that actively follow the motion of the user's arms and do not require the user to slide their forearms over potentially abrasive fixed supports during working motions.

Further objects of the invention will be apparent from review of the disclosure, drawings and description of the invention below.

DISCLOSURE OF THE INVENTION

A torso and forearm supporting device for supporting the body of a user resting in a seated or standing position is provided. The device includes a support base, such as a swivel chair base or foot-rest floor mounted platform. A post assembly is mounted extending upwardly from the base and a torso support pad is disposed on the top end of the post assembly to support the user in a chest-supported position by engaging the user's chest. Alternatively, the torso pad can be used to support the user in a back-supported position by engaging the user's back. Forearm supports allow the user to rest at least one forearm during forearm movement while continuously engaging the armrest.

A seat can be mounted to the base, for seating the user in the chest-supported position straddling the post assembly and also in the back-supported position. Alternatively, the support base can include a foot-rest floor mounted platform and an upright stanchion extending from the floor mounted platform, with a top portion of the stanchion including a post assembly mounting connection.

A preferred configuration includes articulated armrest brackets that fold in a compact manner behind the post assembly for storage when not in use.

A chair configured embodiment of the invention therefore provides for a chest-supported straddle posture chair or front-leaning standing (upright) posture where the pad mounted to the post assembly can be used to engage the chest of the user.

Moreover, the chair is also adapted for conventional office or industrial environments to seat the user at a desk or workstation in a back-supported seating position using the same pad mounted to the post assembly to support the user's back. The forearm supports conveniently fold in a compact unit behind the back of the user. Unlike some of the armrests of the prior art, these forearm supports will not interfere with the usual activities of the user, when not required.

The pedestal on which the seat cushion of the chair rests is fixably or slidably adjustable such that the user can adjust the seat forward or rearwardly along the median line for optimal positioning of the user's centre of gravity relative to the base in either of the seating orientations. The capacity to adjust the seat position prevents the chair from overturning when the user changes position from the chest-supported straddle posture to the traditional back-supported posture using the same seat, pedestal and support base.

Another embodiment of the invention provides torso and forearm support to the user in a standing position. The post assembly can be mounted to an upwardly extending stanchion supported on a floor mounted base. The same post assembly with forearm rests and chest/back pad can be mounted for standing or seated positions on different bases.

An advantage of the invention is the unique combination of a torso support together with individually adjustable forearm supports that continuously engage the forearm of the user and follow the motion of the user's arm within a predetermined transverse plane. A preferred embodiment in the invention, for example, includes an articulated linkage that supports the forearm of the user within a plane that is transverse to the post assembly. Individual adjustments of the two arm rests are permitted with sliding adjustment on the post assembly and rotational adjustments to suit the particular position of each arm required by the operation carried out by the user.

A distinct advantage of the invention is the ability of the linkage members to fold together in overlapping relation into a compact unit that is retained behind the post assembly when not in use. In contrast, many of the prior art armrests are quite inconvenient and interfere with normal use of the chair when a specific support in a specific position is not required.

Further advantages of the invention will be apparent from the following detailed description and accompanying drawings.

DESCRIPTION OF THE DRAWING

In order that the invention may be readily understood, one embodiment of the invention is illustrated by way of example in the accompanying drawings.

3 with the exception that the second embodiment does not include rotational adjustment of the forearm support bracket about a generally horizontal axis.

Figure 1:
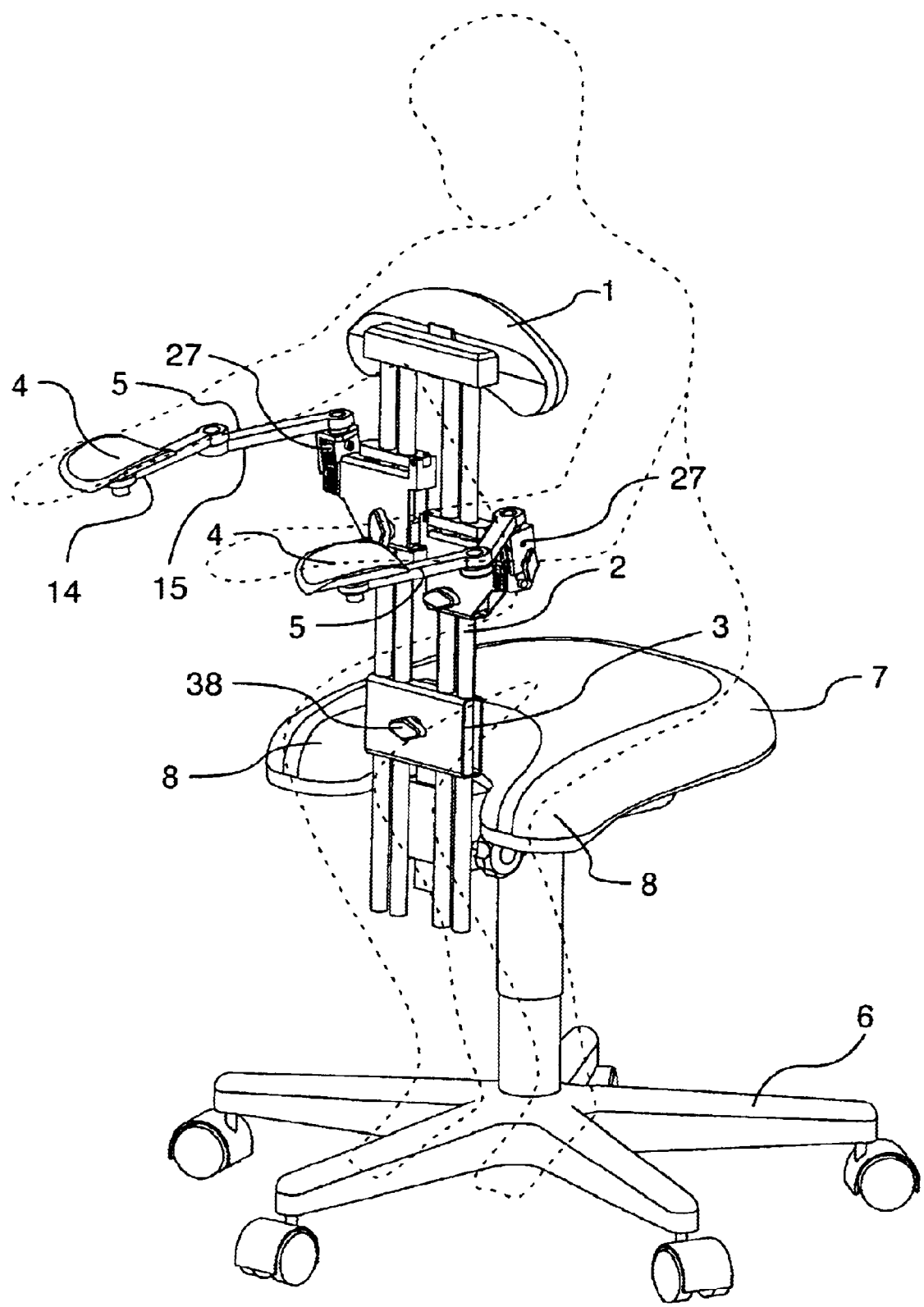
FIG. 1 is a perspective view (of a first embodiment of the invention) wherein the user is shown in dashed outline while seated in the chest-supported straddle posture position with chest resting on the pad at the top end of the post assembly, and forearms each resting on independently adjustable armrests that continuously engage the forearms during arm motion in planes transverse to the post assembly.
Figure 6:
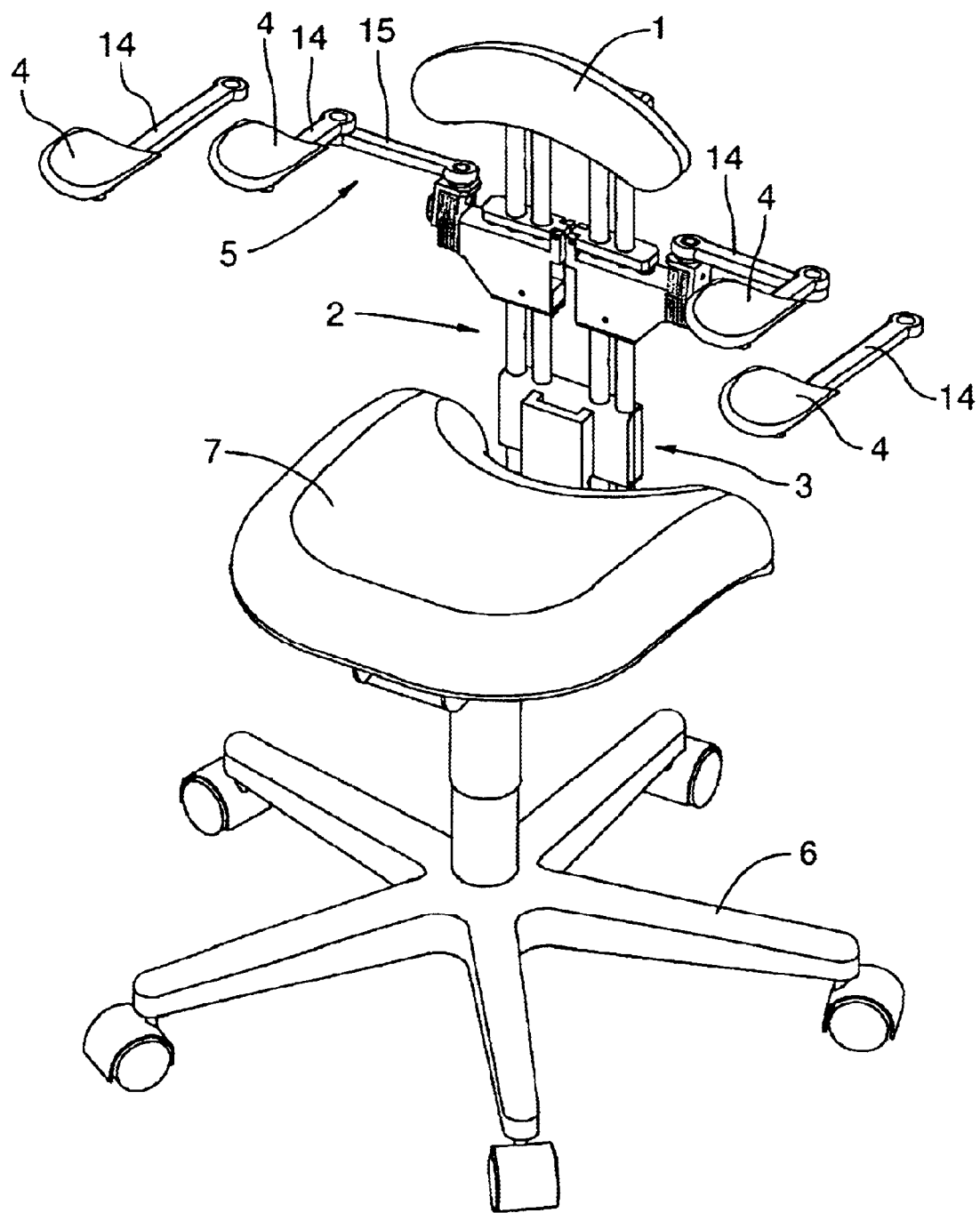

FIG. 6 is a perspective view (of the first embodiment) similar to that of FIG. 1 except with the brackets and armrests swung about to support the elbows and forearms of the user seated in the back-supported position, and also including optional outer linkage members of increased length for this purpose.

Figure 7:
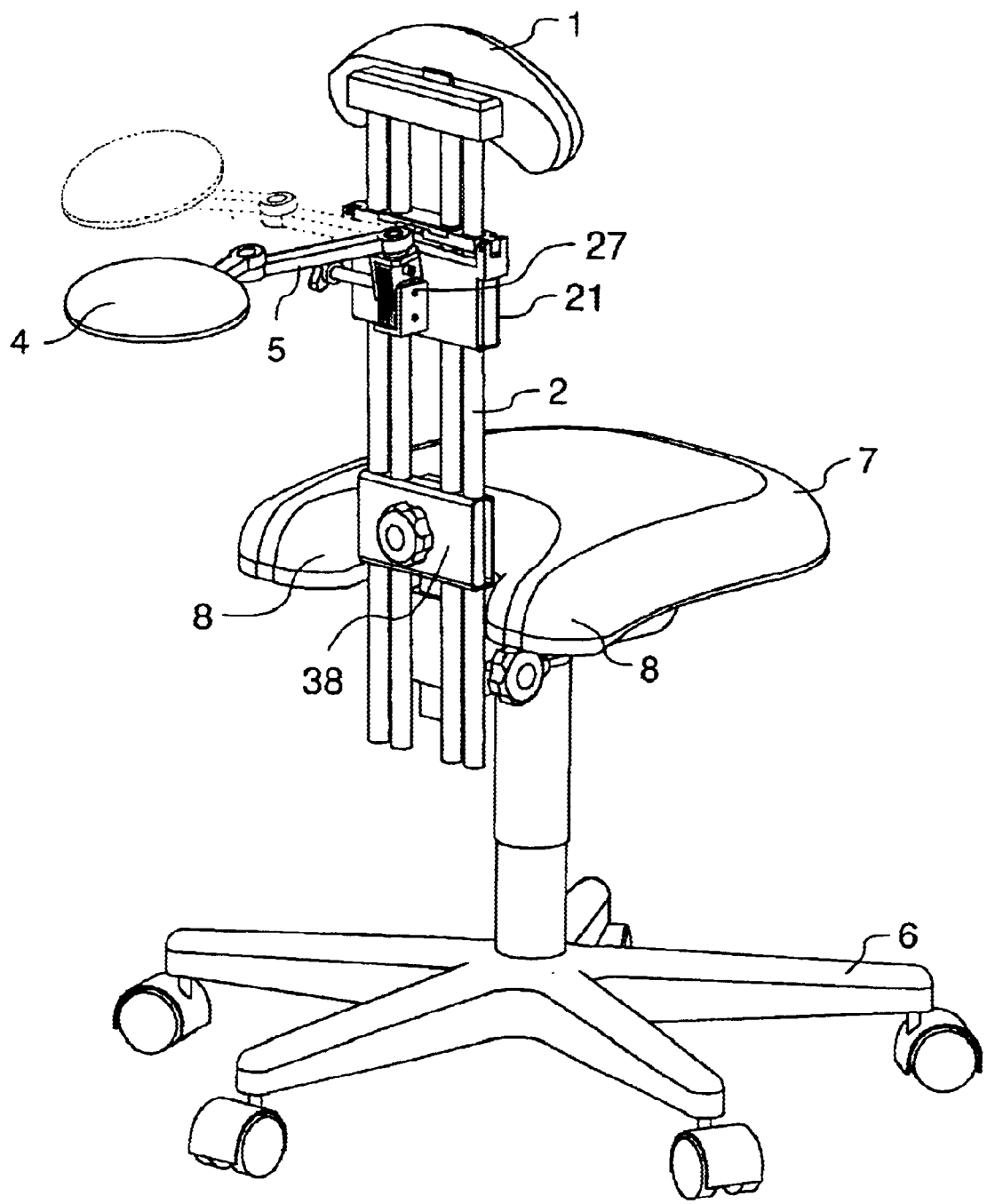

FIG. 7 is a rear perspective (of a third embodiment) generally as in FIG. 1, showing a single centrally-mounted forearm support rather than the two opposing supports shown in FIG. 1.

Figure 8:
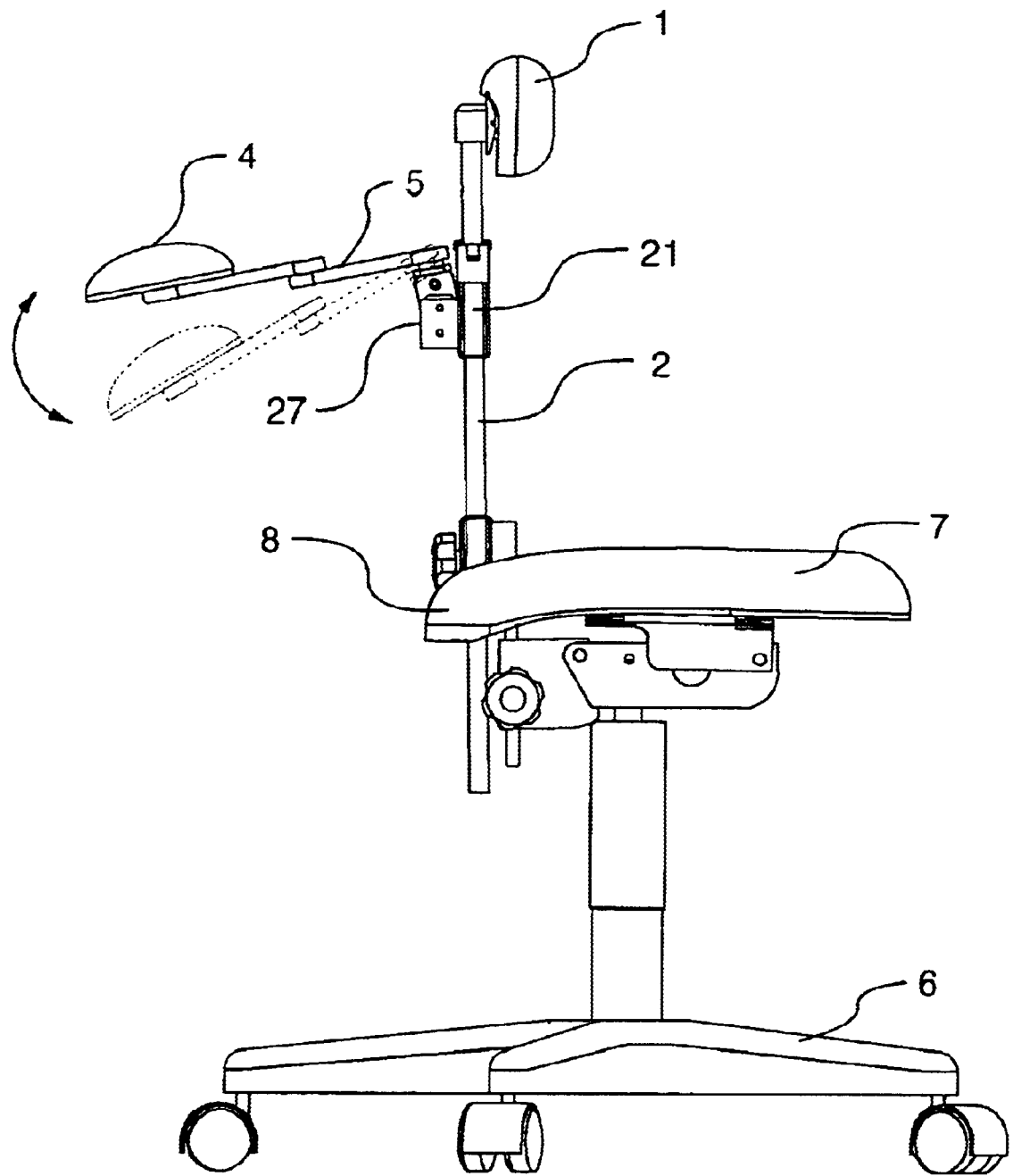

FIG. 8 is a side view (of the third embodiment) of FIG. 7 indicating the capacity for rotational adjustment about a horizontal axis.

Figure 9:
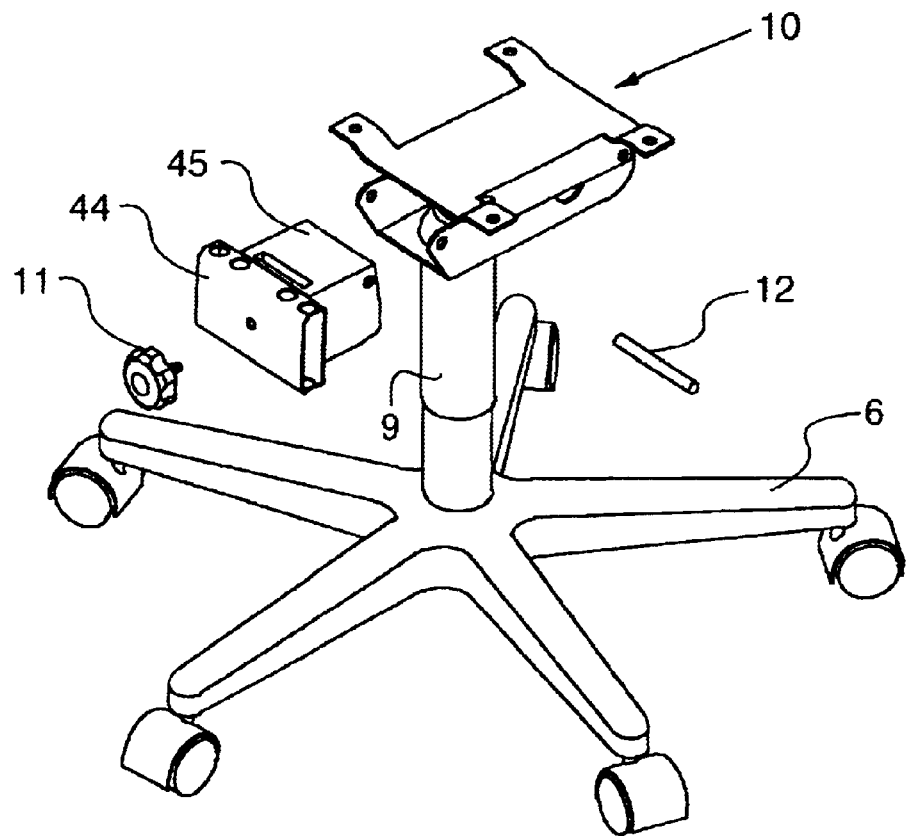

FIG. 9 is an exploded perspective view of a swivel chair base (applicable to first, second and third embodiments) showing details of the post assembly mount used to secure the four tubes of the post assembly to the pedestal of the swivel chair base.

Figure 10:
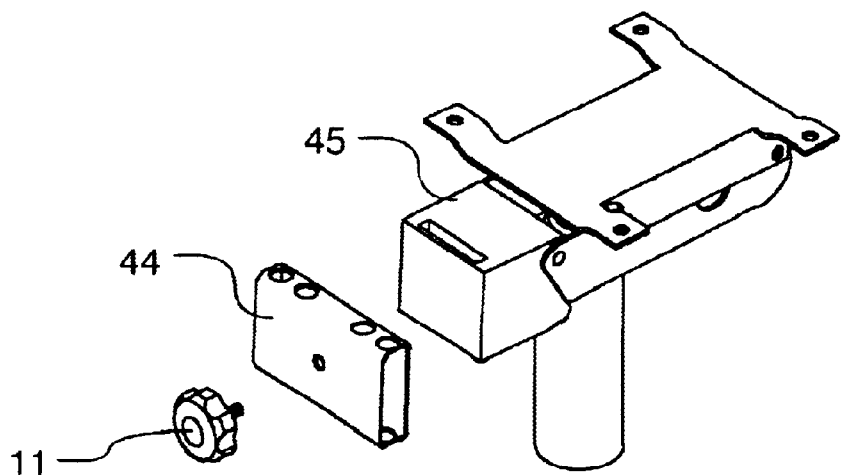

FIG. 10 is an exploded perspective view similar to FIG. 9 but showing a retrofit alternative for welding a post mount assembly to an existing swivel chair base.

Figure 11:
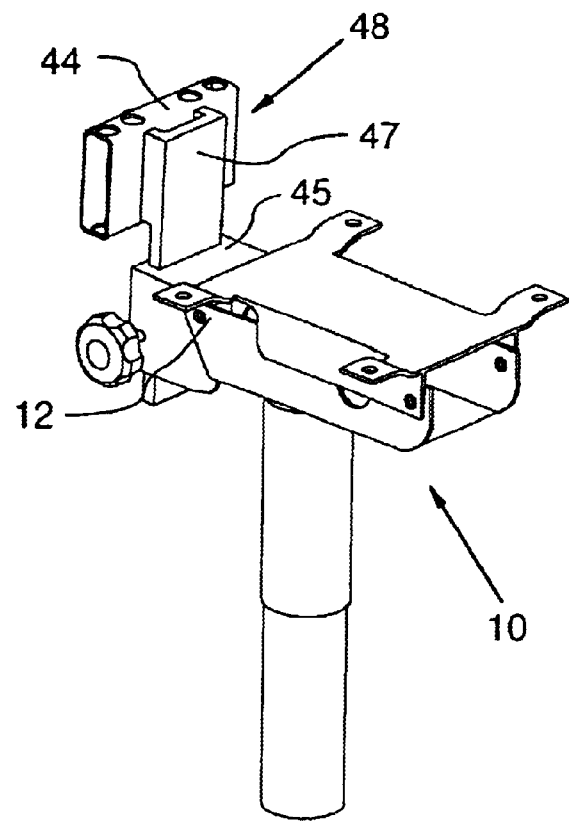
Figure 12:
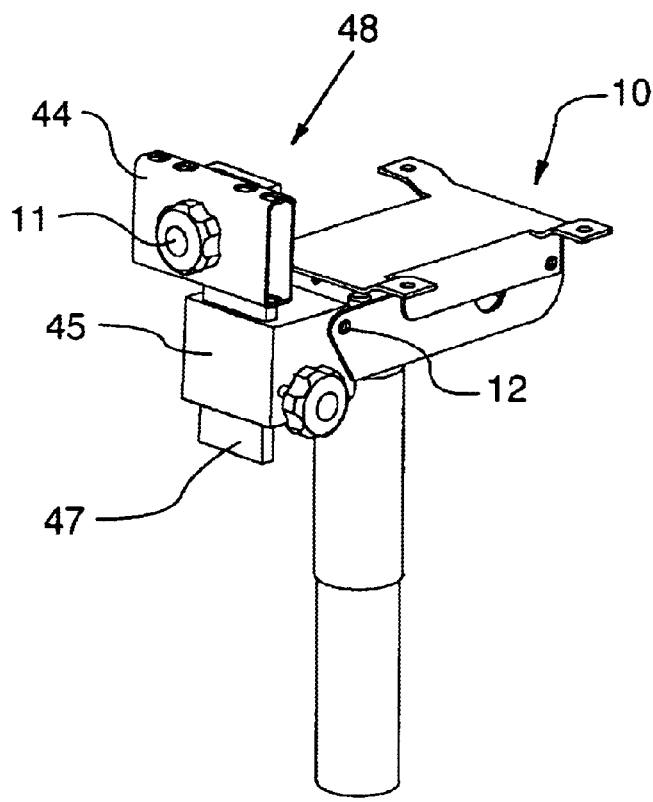

FIGS. 11 and 12 are perspective views (applicable to first, second and third embodiments) showing a retrofit alternative post assembly mount with a downwardly extending tongue adapted to be retained in a conventional seat back mount of a swivel chair base.

Figure 13:
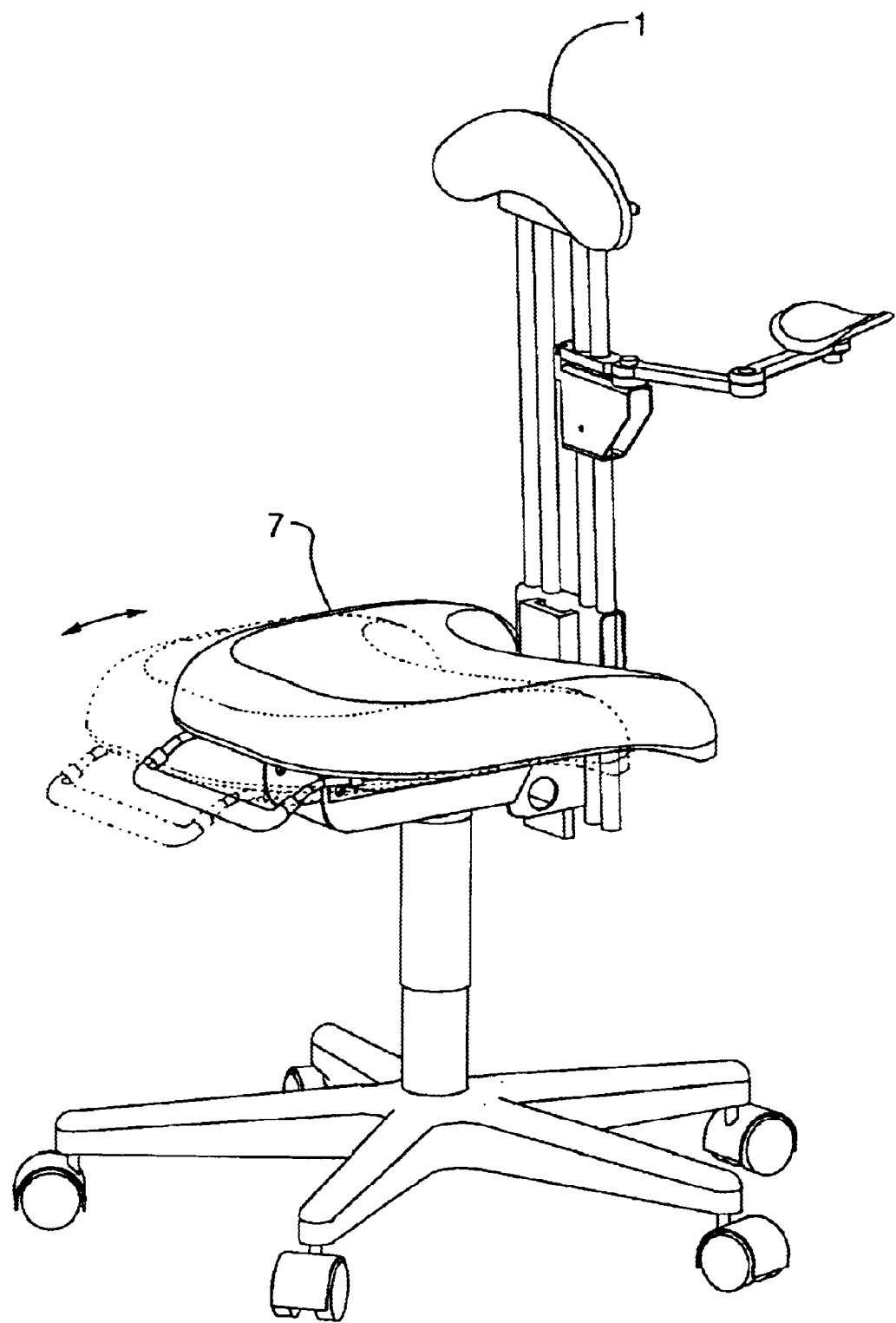

FIG. 13 shows a slidable seat platform on the pedestal that allows the user to manually adjust to an optimal centre of gravity relative to the swivel base.

Figure 14:
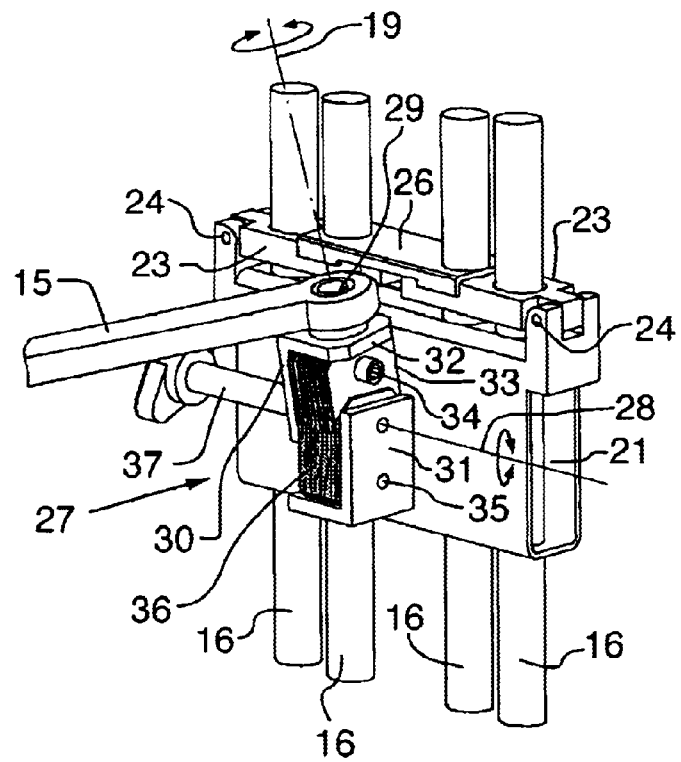

FIG. 14 is a detailed rear perspective view (of the third embodiment) showing details of the mounting of the armrest bracket to the post assembly permitting vertical sliding adjustment relative to the post assembly and rotation adjustment about a horizontal axis.

Figure 15:
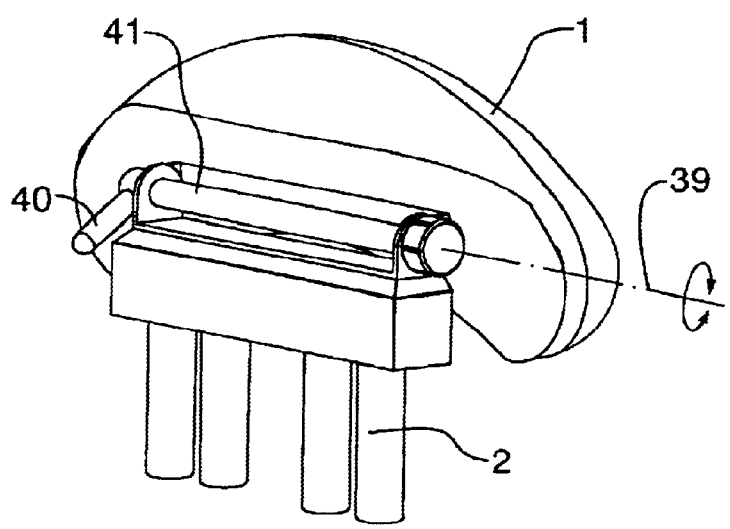

FIG. 15 is a detailed perspective view (applicable to all embodiments) of the mounting of the torso supporting (i.e. chest and back) pad connected to the top end of the post assembly to permit horizontal rotational adjustment.

Figure 16:
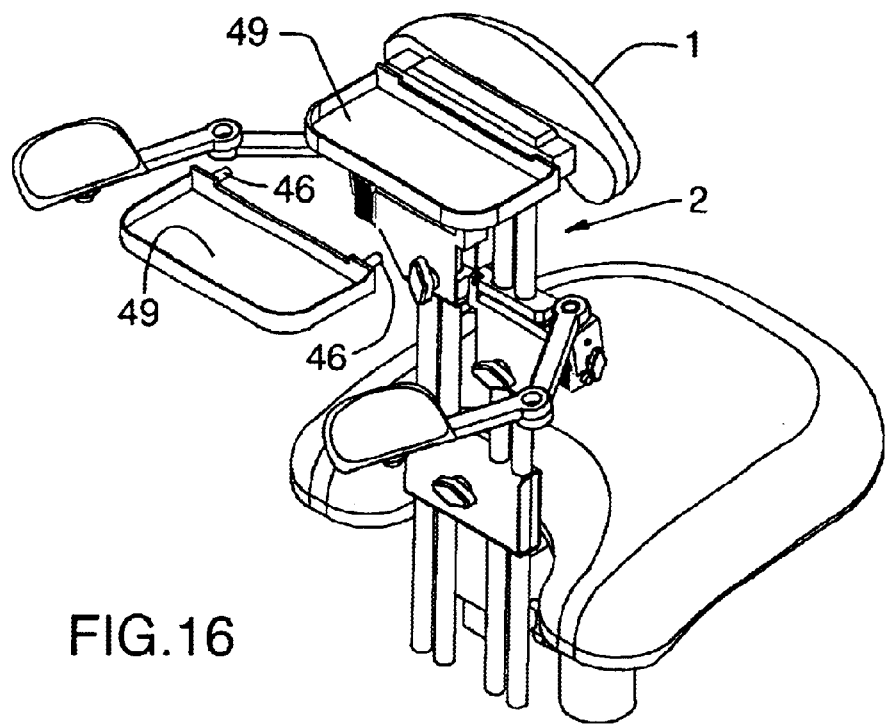

FIG. 16 is a perspective view (of a first embodiment of the invention) with a removable tray secured with pins to the top end of the post assembly.

Figure 17:
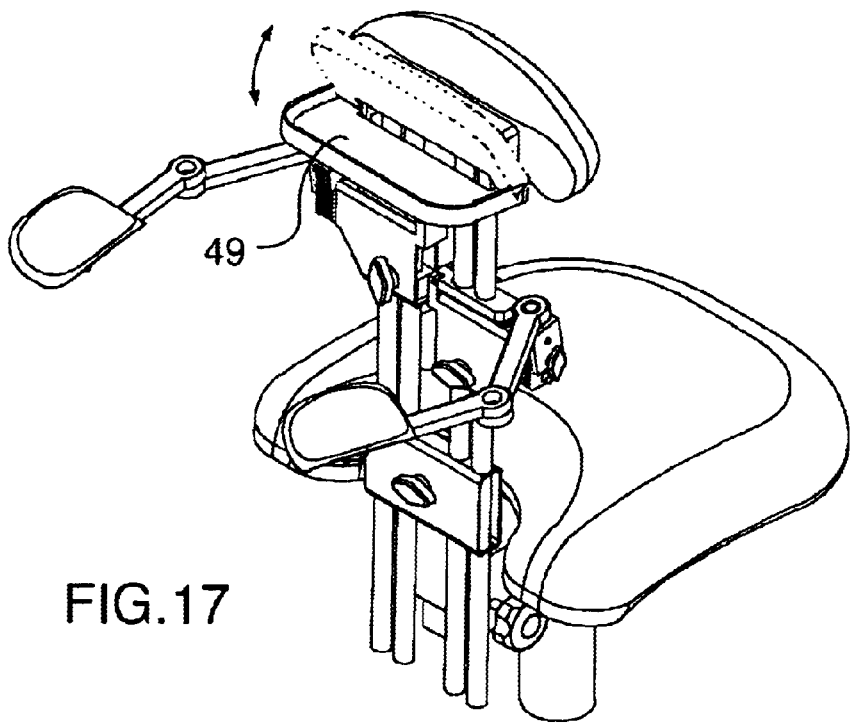

FIG. 17 is a like perspective view (of a first embodiment of the invention) with a hinged tray secured to the top end of the post assembly.

Figure 2:
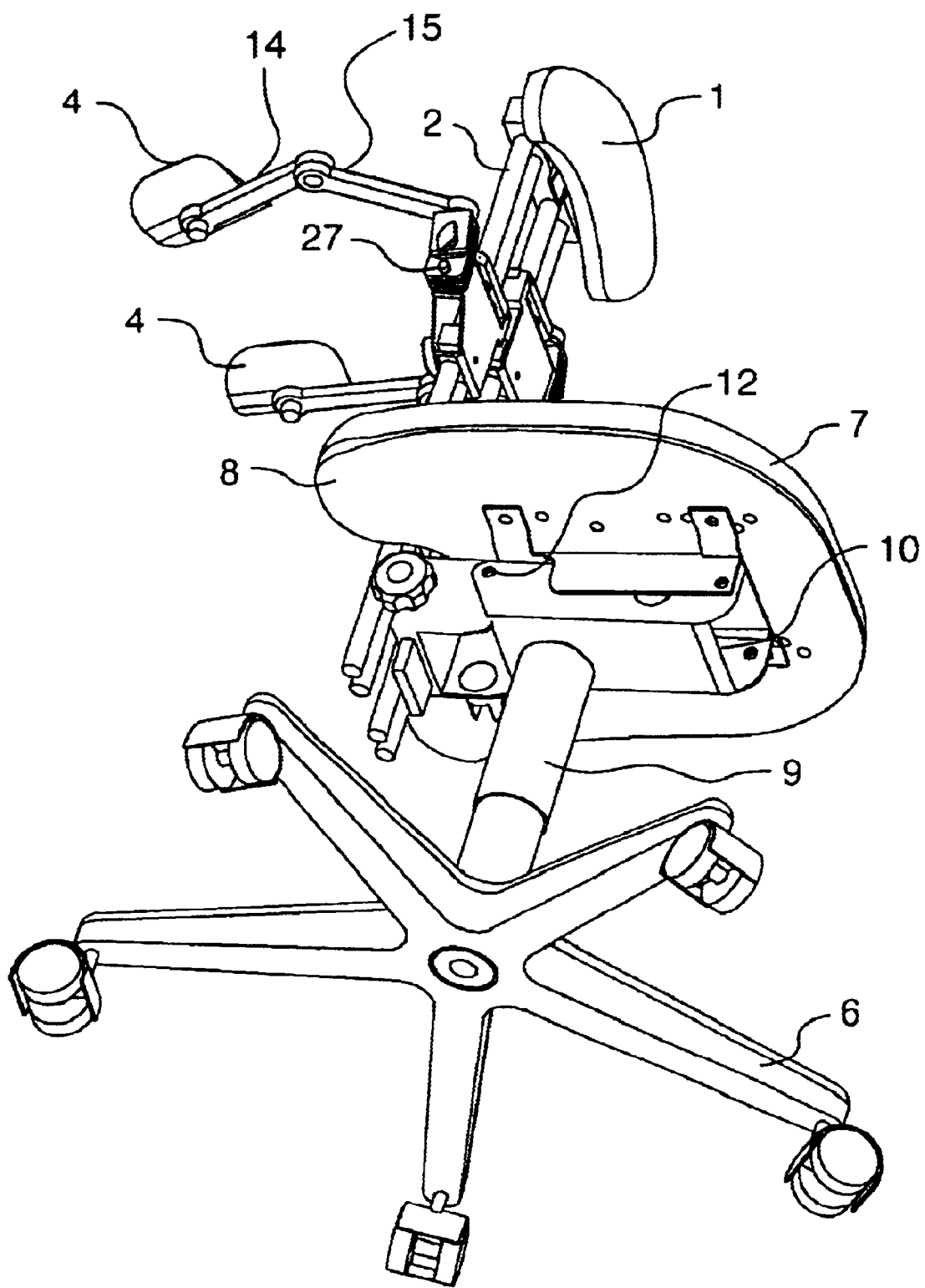
FIG. 2 is a bottom perspective view (of the first embodiment) showing the adjustable base and post assembly mounting and the underside mounting of the seat, with optional rearwardly extending thigh support segments used in the chest-supported straddle posture position.
Figure 18:
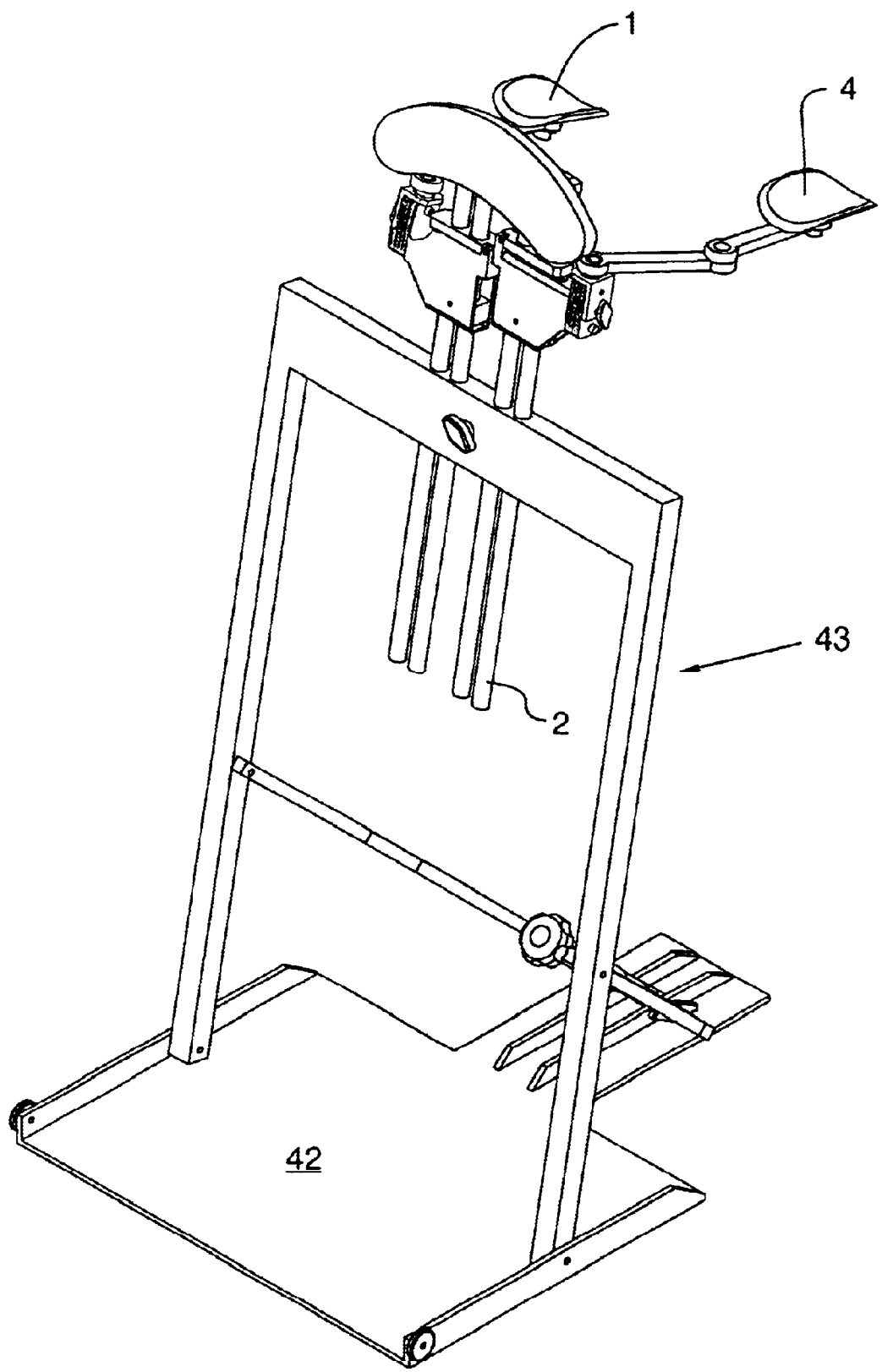
Figure 19:
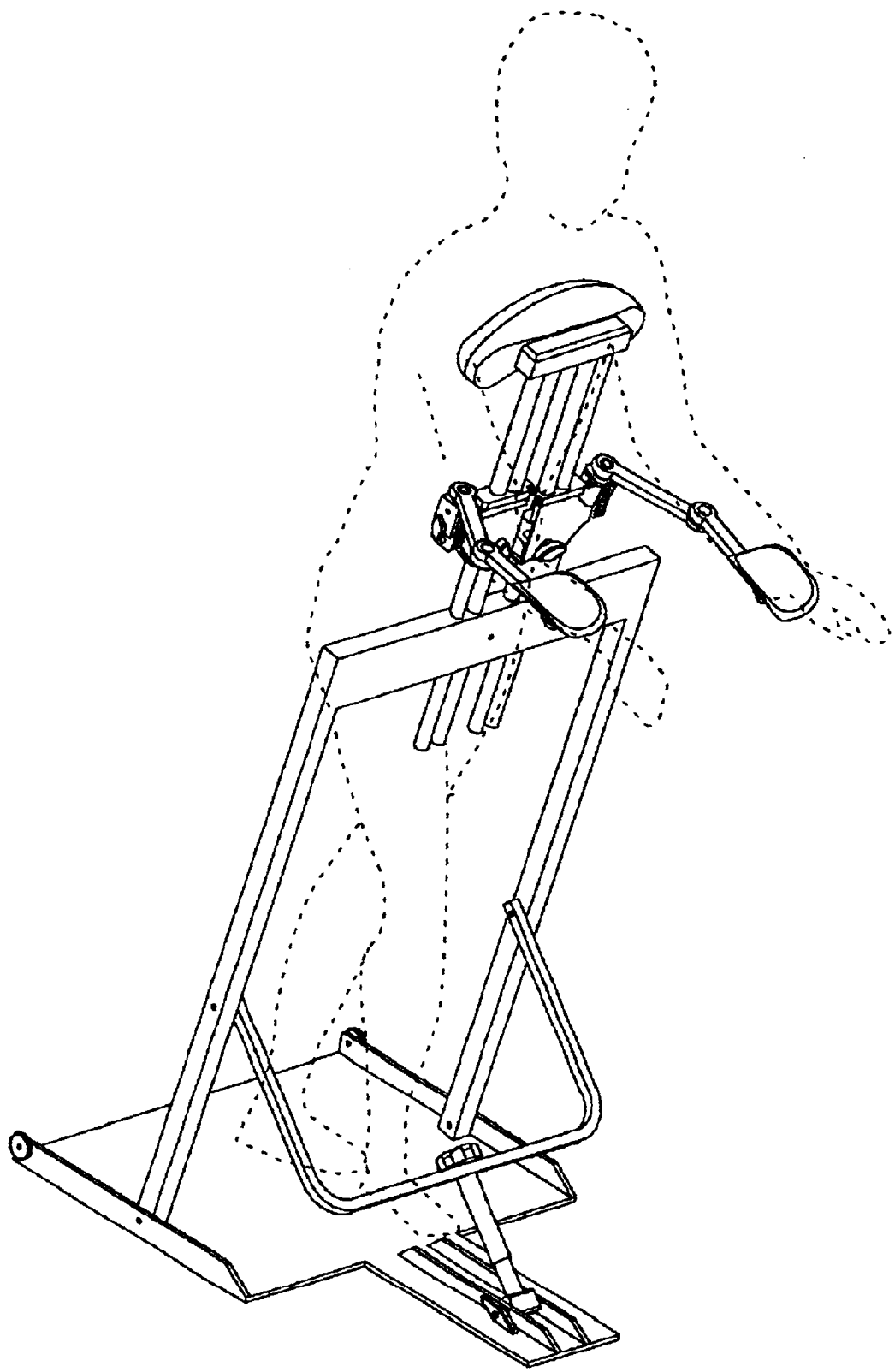

FIGS. 18 and 19 show perspective views (of a fourth embodiment) of the invention adapted for use in a standing position with or without a footrest floor mounted platform and stanchion supporting a post assembly, brackets and armrests similar to those shown in FIG. 1 and 2.

Figure 20:
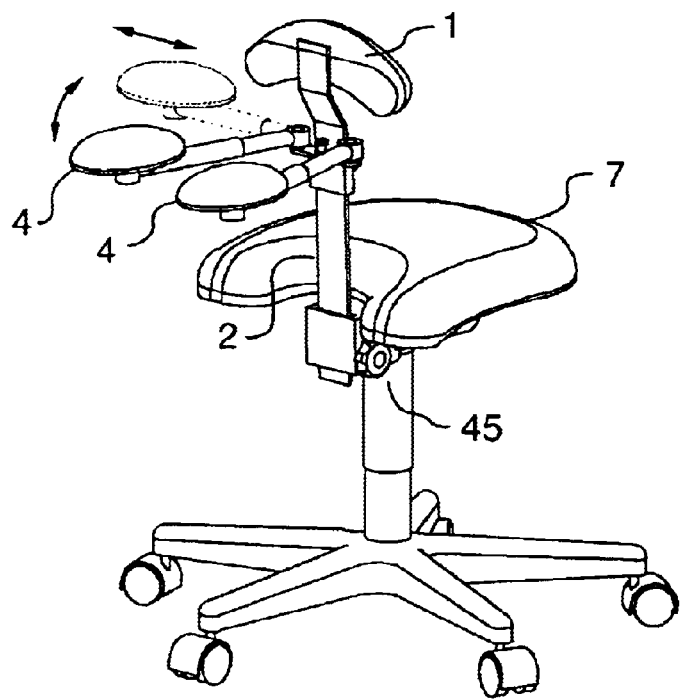
Figure 21:
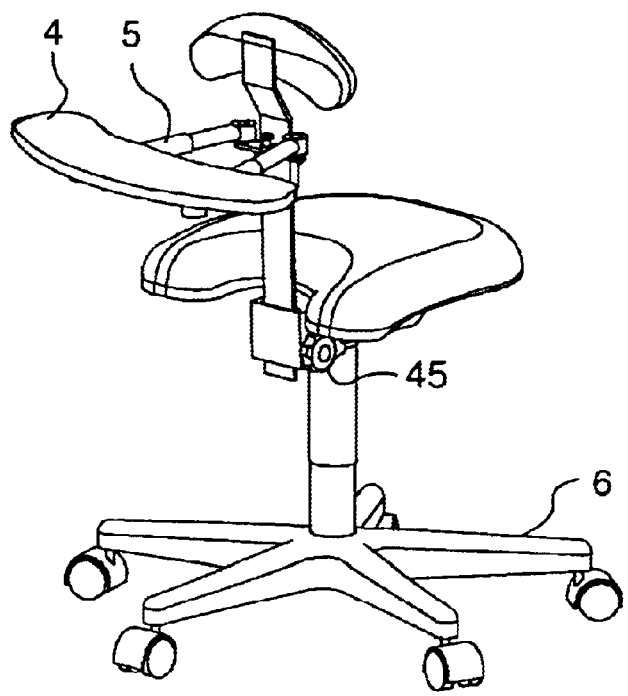

FIGS. 20 and 21 show perspective views (of a fifth embodiment) of the invention with a telescoping and pivoting bracket supporting one or two armrests respectively, and slidably supported on a single flatbar post.

Figure 22:
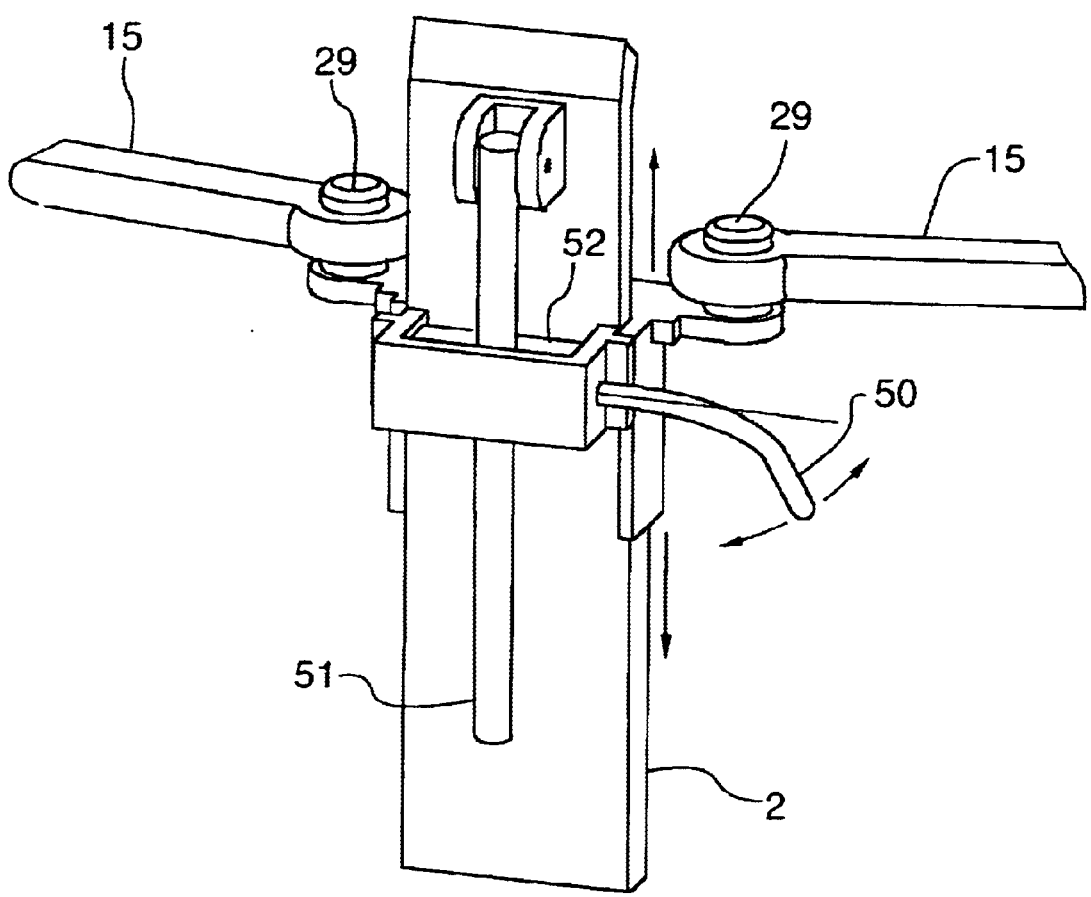

FIG. 22 shows a detail view of the vertical adjustment device adapted for the flatbar post of FIGS. 20 and 21.

Further details of the invention and its advantages will be apparent from the detailed description included below.

DETAILED DESCRIPTION OF PREFERRED EMBODIMENTS

FIG. 1 shows a perspective view of the first embodiment of the invention with the user in dashed outline seated in a chest-supported straddle position. The user's chest rests on a pad 1 at the top end of a post assembly 2 made of four parallel tubes 16 (in the first embodiment illustrated). The height of the pad 1 can be adjusted linearly relative to the seat 7 with a sliding connection 3 with thumbscrew clamping mechanism.

The forearms of the user rest on independently adjustable armrests 4 that continually engage the users forearms during arm motion in a plane that is transverse to the post assembly 2. The first embodiment illustrated in FIGS. 1–4 includes articulated brackets 5 constructed of two rotatably connected links 14, 15 that will be described in detail below together with their vertical and rotational adjustment features.

The torso and forearm supporting device can be supported on any type of base including a swivel chair base 6 of a conventional type (as shown in FIGS. 1–2 for example) with adjustable vertical positioning of the seat 7, and on a standing version (as shown in FIGS. 18–19).

In the chair-type embodiment, the seat 7 can optionally include two rearwardly extending thigh supporting segments 8 that surround the lower portion of the post assembly 2 and enable the user to comfortably straddle the post assembly 2 while leaning forward on the pad 1 with the chest for support. In the workstand embodiment illustrated in FIGS. 18–19, the torso and forearm supporting device can be supported on a floor mounted footrest with foldable stanchion 43 extending upwardly from the floor.

FIG. 2 shows an underside perspective view of the base 6 with telescoping adjustable stand 9 that supports a pedestal 10. Other suitable adjustable stands 9 include gas cylinders or screw posts. FIG. 9 shows details of the pedestal 10 with a post assembly mount 44 having four vertical bores for slidably securing the four tubes 16 of the post assembly 2. Thumbscrew 11 provides a lock and release mechanism for the sliding motion of the four parallel tubes 16 secured by the post assembly mount 44. The post assembly mount 44 is welded to the pedestal mount 45, and can rotate about pin 12 using conventional spring loading. FIG. 10 indicates that a conventional swivel chair pedestal 10 can be retrofit by welding a mount 44 to the slotted end piece 45

FIGS. 11 and 12 show an alternative configuration of the post assembly mount 44. In this configuration, a flatbar tongue 47 is welded to the post assembly mount 44. The retrofit unit 48 can be inserted into the slotted end piece 45 of a conventional swivel chair.

FIG. 13 shows a slidable seat platform 49 secured to the pedestal. The manual adjustment by the user of the seating position relative to the base and the post assembly 2 allows the user to be seated properly relative to the base with the centre of gravity of the user's body positioned to avoid overturning the base when leaning on the chest supporting pad 1. The centre of gravity of the user and the force applied to the back resting or chest resting pad 1 differs between the back-supported seating position and chest-supported straddle seating position. The sliding motion provided by slidable seat 7 thus compensates for variations in the user's weight distribution when the user moves from a chest-supported position to a back-supported seating position.

Figure 3:
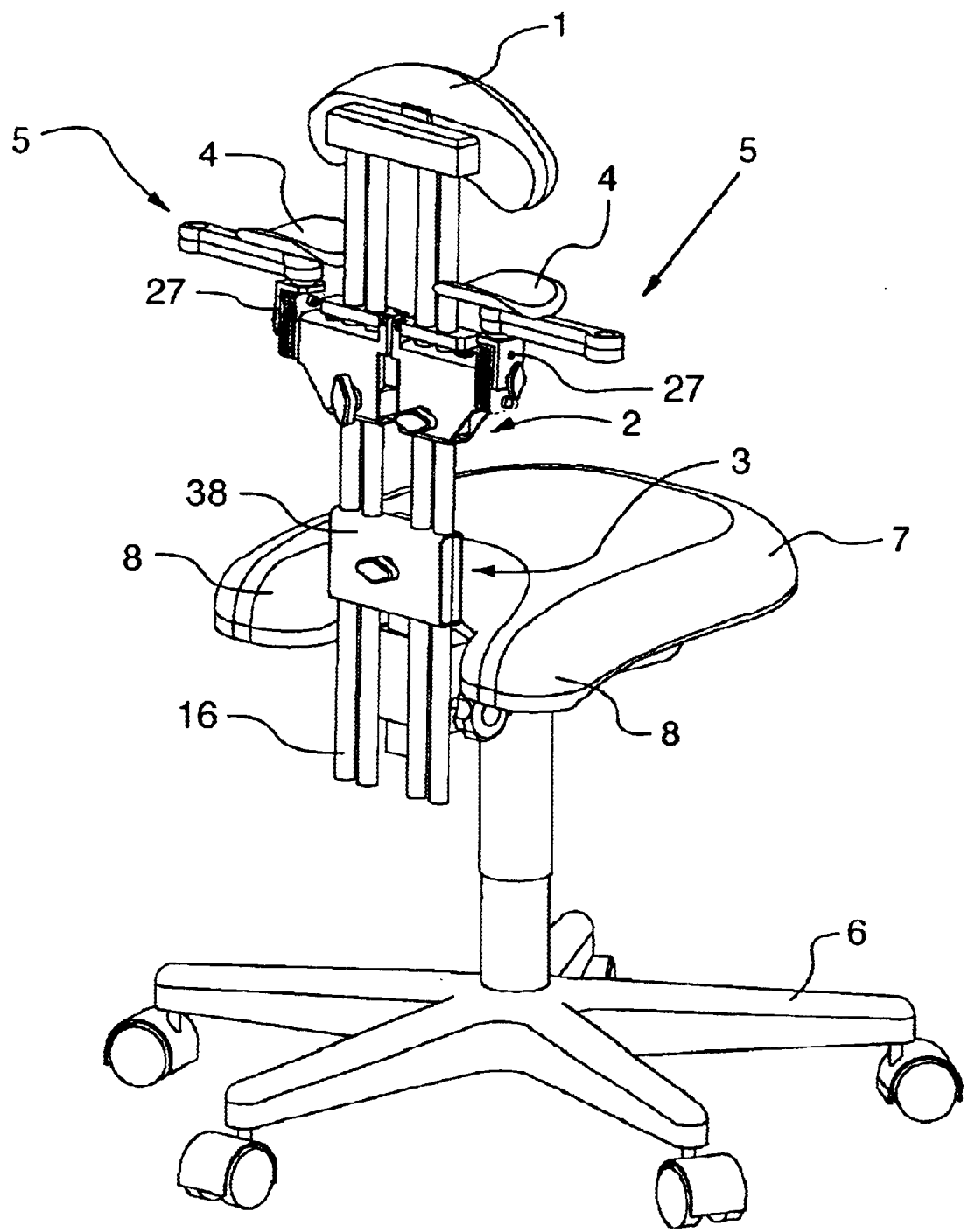
FIG. 3 is a perspective view (of the first embodiment) showing the armrests folded together in overlapping relation into a compact unit behind the post assembly when not in use.
Figure 4:
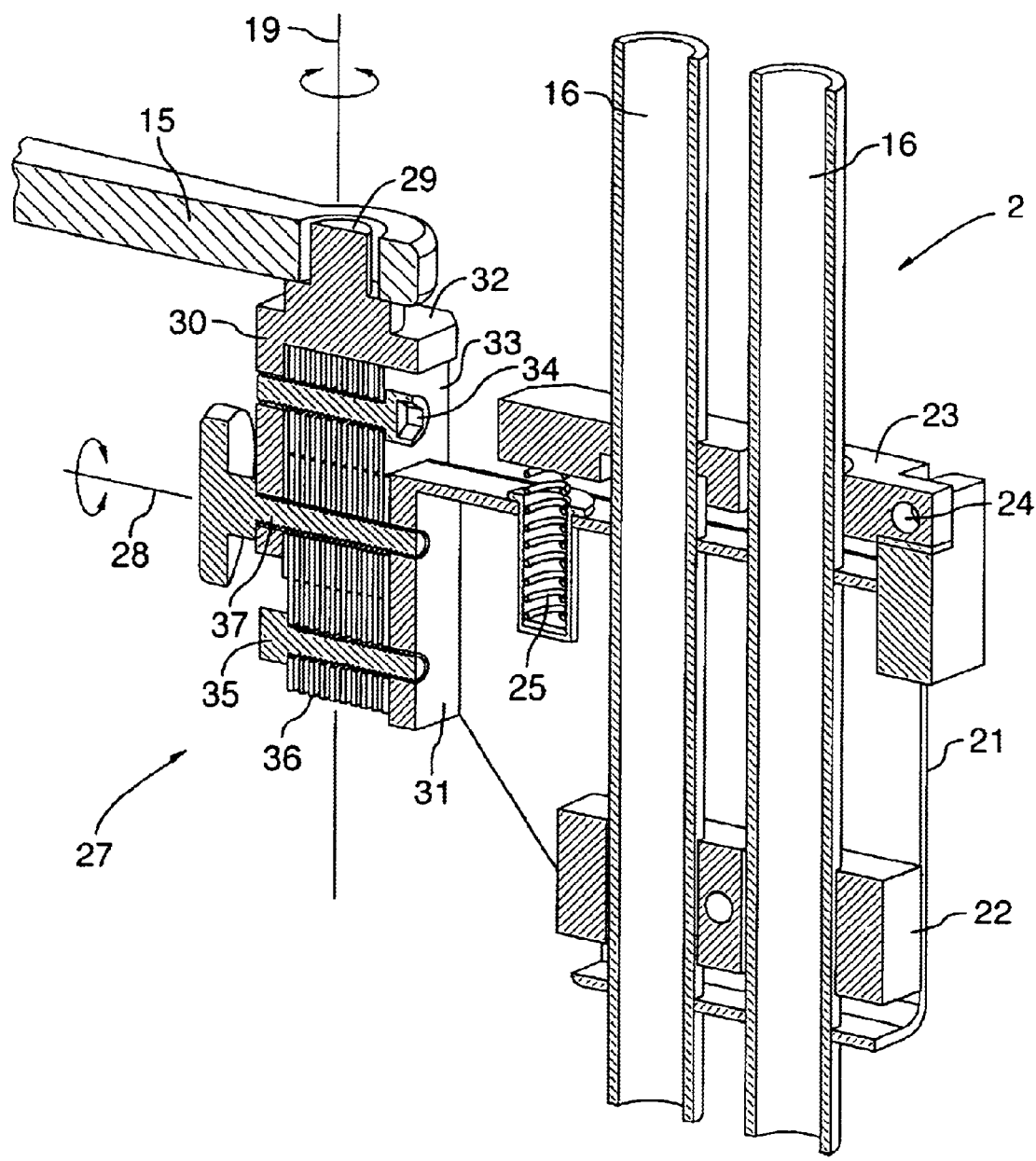
FIG. 4 is a vertical cross-section view (first embodiment) through one side of the post assembly and through the rotatable connection between the articulated bracket and the post assembly that permits independent rotational and sliding adjustment of the armrest support relative to the supporting post assembly.
Figure 5:
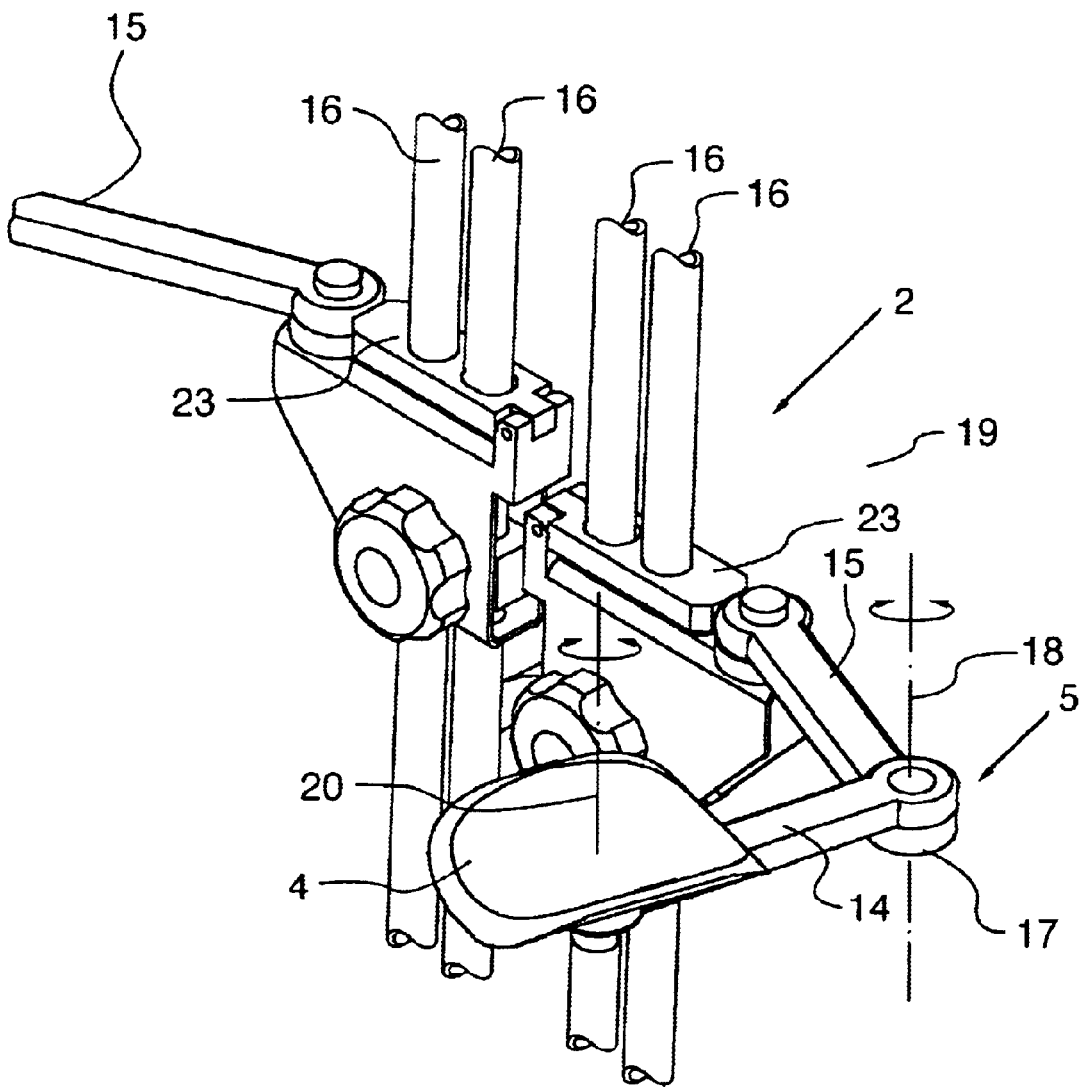
FIG. 5 is a detailed rear perspective view (of a second embodiment) of two sliding connections between the forearm support and post assembly, generally as shown in FIG.

FIG. 5 shows details of the forearm supports and adjustable connection to the post assembly 2, and FIG. 4 shows details of the rotatable connection 27. It should be noted that FIG. 3 shows a first embodiment of the invention with rotational adjustment connection 27 whereas FIG. 5 shows a second embodiment without rotational adjustment. In all other aspects FIGS. 4 and 5 show the same vertical sliding connection and relate to the same articulated forearm support as will be described below.

As is apparent from FIG. 1 and FIG. 5, the arm rest 4 continuously engages the forearm of the user while seated in the chest-supported straddle seating position. The pivot connection between the linkage members 14 and 15 enables the user while resting their forearms in the armrest 4 to extend and retract the articulated bracket 5 within a predetermined plane that is transverse to the post assembly 2. It will be appreciated that although all drawings show a post assembly 2 comprised of four parallel tubes 16, the invention is not limited to any particular mechanical arrangement shown and various other mechanical equivalents are within the scope of the invention.

Therefore in its broadest aspect, the invention comprises a torso and forearm supporting device as shown in FIGS. 1 and 2 that can also be easily adapted to a back-supported seating position used for example in general office environments. The chest-supported straddle posture as shown in FIG. 1 is contemplated as being most useful in industrial or medical environments where people are required to hold their posture and arms in certain suspended positions for prolonged periods of time. The chair has a support base 6 that includes a vertically adjustable stand 9 and pedestal 10. The seat 7 supports the user and is fixably or slidably mounted to the pedestal 10 of the base 6 (as indicated in FIG. 13).

The torso of the user is supported with a pad 1 disposed at the top end of the post assembly 2. The user is supported in chest-supported straddle position as shown in FIG. 1 by engaging the chest on the pad 1 and is supported in back-supported position with the pad 1 engaging the back of the user approximately in the area below the shoulder blades. In the back-supported position, the armrests 4 can be positioned laterally (see FIG. 6) to support the user's elbows as well. If not required, the brackets 5 can fold up as shown in FIG. 3.

The user supports one or both forearms on the arm rests 4 mounted on articulated brackets 5 (made of linkage members 14 and 15) such that the user's forearm during movement is continuously and dynamically engaged in an armrest 4 while seated in the chest-supported straddle seating position as shown in FIG. 1. As indicated in FIG. 13, the linkage members 14, 15 can also swing around to support the elbows and forearms of the user on the armrests 4 laterally positioned on the sides of the user while seated in the back-supporting position resting the users back against the pad 1.

In general the forearm support comprises an armrest 4 mounted to the outer end of a movable articulated bracket 5 with the inner end of the linkage member 15 secured to the middle portion of the post assembly 2 and extending transversely from the post assembly 2. The articulated bracket 5 is retractable towards and extendable from the post assembly 2 within a predetermined transverse plane for each of the armrest 4 and articulated bracket 5 assemblies. For example, in the embodiments shown in FIGS. 1, 2 and 4, the brackets 5 are independently adjustable in relation to the post assembly 2. In the embodiment shown in FIGS. 1–4 the brackets 5 are also rotationally adjustable relative to the post assembly 2. Although the drawings show an articulated linkage having linkage members 14 and 15 in an axial series, the articulated bracket 5 also includes equivalent mechanisms that extend and retract within a predetermined transverse plane. For example, the brackets 5 may also comprise telescoping arrays of coaxial tubular members (see FIGS. 20–21), or a parallel motion linkage assembly to equal advantage. A preferred feature of any articulated bracket 5 assembly is the capacity to collapse into a compact unit (see FIG. 3) for storage thus avoiding interference with the user when not required.

As best shown in the embodiment illustrated in FIG. 5 the articulated bracket 5 comprises of an inner linkage member 15 that is rotatably joined with a hinge 17 to an outer linkage member 14 with an axis of rotation 18 that is perpendicular to the transverse plane within which the linkage 14 and 15 operates. In a like manner, the articulated bracket 5 is rotatably mounted to the post assembly 2 with an axis of rotation 19 also perpendicular to the transverse plane of operation. The armrest 4 is rotatably mounted to the articulated bracket 5 also with an axis of rotation 20 perpendicular to the transverse plane.

As can be appreciated from viewing FIGS. 2, 3 and 5, the use of linkage members 14 and 15 enables the articulated bracket 5 to fold together in overlapping relation adjacent to the post assembly 2 when not in use. For example, if a dentist or surgeon wishes to use the chair for surgery or dental operations, they can take the chest-supported straddle position shown in FIG. 1 and rest their forearms on the armrests 4 during prolonged periods of time in the same position. However, when the chair is not being used in this manner, it may be deployed for general office type seating at a desk or workstation. The articulated bracket 5 with folding linkages 14 and 15 can be conveniently folded up and retained behind the post assembly 2 when the user adopts the back-supported seating position or alternatively while in the chest-supported straddle seating position when total freedom of movement of their arms is desired.

As indicated in the sectional view of FIG. 4 and perspective view of FIG. 5, the connection between the inner end of the articulated bracket 5 and the middle portion of the post assembly 2 is preferably linearly adjustable to accommodate the desired height of the armrest 4 set by individual users. In the embodiments shown, the housing 21 (in FIG. 4) includes a sliding block 22 and a lever 23 hinged at pin 24 and biased to an upper locking position with spring 25. To rapidly adjust the vertical positioning of the housing 21 on two tubes 16 of the post assembly 2, the user presses a thumb against the outward end of the lever 23 against the biasing force of the spring 25 to free the housing 21 to slide vertically relative to the tubes 16. When the lever 23 is released, the spring 25 forces the lever 23 to frictionally bind at an angle against the outer holes of the tubes 16 thereby rapidly locking the housing 21 and the brackets 5 and armrest 4 in position. In the third embodiment illustrated in FIG. 14, both levers 23 can be depressed simultaneously with the application of manual pressure on sliding cover plate 26.

The first embodiment of the invention illustrated in FIGS. 1–4 includes a rotatably adjustable connection 27 between the inner end of the articulated bracket 5 and the middle portion of the post assembly 2. The rotatably adjustable connection 27 has an axis of rotation 28 that is parallel to the transverse plane within which the brackets 5 operate. The third embodiment shown in FIGS. 7, 8 and 14 includes an identical rotatably adjustable connection 27 that mounts a single articulated bracket 5 with inner linkage member 15 mounted to rotate about axis 19.

With reference to FIGS. 4 and 14, the construction of the rotatably adjustable connection 27 will be described. The inner end of inner linkage member 15 is mounted on a pin 29 (FIG. 13) that extends from a top plate 32 of an upper clamping plate 30. A plurality of laminated upper plates 33 are connected to the upper clamping plate 30 and are restrained from rotation by physical contact with the top plate 32 secured in place with bolt 34. In a like manner the lower plate 31 and bolt 35 restrain an alternating series of lower laminated plates 36. The clamping bolt 37 is threaded into the lower plate 31 and extends through the alternating laminated plates 33 and 36.

When the clamping bolt 37 is tightened, the upper clamping plate 30 is forced toward the lower clamping plate 31 and the multiple laminated plates 33 and 36 are clamped together. A significant degree of friction between the faces of laminated plates 33 and 36 is developed to quickly and securely clamp the position of linkage member 15 in an angular position rotating about axis 28.

The post assembly 2 is connected to the base 6 with an adjustable sliding connection 38 that can be manually clamped with a thumbscrew.

Further as shown in FIG. 15, the pad 1 is connected to rotate about axis 39 while connected to the top portion of the post assembly 2. A clamping lever 40 threads on a bolt 41 to quickly and simply secure the pad 1 in position relative to the post assembly 2. Optionally, FIG. 16 shows a removable tray 49 secured with pins 46 to the top end of the post assembly 2. FIG. 17 shows a like tray 49 hinged to the top end of the post assembly 2.

FIGS. 20–22 show a fifth embodiment with a flatbar post 2 adapted to slide into the slotted end piece 45 of a standard swivel chair base 6. As seen in FIG. 22, to accommodate the flatbar post 2, a vertically slidable connection is provided wherein rotation of lever arm 50 releases hanging rod 51 from binding engagement with an aperture in plate 52.

Therefore the invention can be adapted to various seated and standing positions with different combinations of elements and configurations as described and illustrated herein. The chest support pad 1 can be combined with one or two forearm support articulated brackets 5 and armrests 4, in a seated position or in a standing position.

Although the above description relates to a specific preferred embodiment as presently contemplated by the inventor, it will be understood that the invention in its broad aspect includes mechanical and functional equivalents of the elements described herein.

We claim:

1. A torso and forearm supporting device for supporting the body of a user resting thereon, the device comprising:
    a support base;
    a post assembly having a top and bottom end, the post assembly extending upwardly from the base;
    torso support means, comprising a pad disposed on the top end of the post assembly, for supporting the user in a chest-supported position by engaging the user's chest and for supporting the user in a back-supported position by engaging the user's back; and
    forearm support means for supporting at least one forearm of the user during forearm movement while continuously engaging an armrest mounted to an outer end of a bracket, an inner end of the bracket secured to a middle portion of the post assembly with a linearly slidable adjustable connection and extending transversely therefrom, the bracket being retractable toward and extendible from the post assembly within a predetermined transverse plane, including a rotatably adjustable connection between the inner end of the bracket and the middle portion of the post assembly, the rotatably adjustable connection having an axis of rotation parallel said transverse plane.

2. The device according to claim 1 including sitting support means, comprising a seat mounted to the base, for seating a user in the chest-supported position straddling the post assembly and in the back-supported position.

3. The device according to claim 1 wherein the post assembly is attached to the top portion of an upwardly extending stanchion resting on a floor platform.

4. The device according to claim 1 wherein the bracket comprises a mechanism selected from the group consisting of an articulated linkage having linkage members in an axial series, a telescoping array of coaxial tubular members, and a parallel motion linkage assembly.

5. The device according to claim 4 wherein the bracket comprises an inner linkage member rotatably joined to an outer linkage member for rotation about an axis perpendicular to said transverse plane.

6. The device according to claim 5 wherein the inner and outer linkage members can fold together in overlapping relation adjacent to the post assembly.

7. The device according to claim 1 wherein the bracket is rotatably mounted to the post assembly for rotation about an axis perpendicular to said transverse plane.

8. The device according to claim 1 wherein the armrest is rotatably mounted to the bracket for rotation about an axis perpendicular to said transverse plane.

9. The device according to claim 1, wherein the linearly adjustable connection has a linear axis aligned relative to the upwardly extending post assembly.

10. The device according to claim 1 wherein the post assembly is connected to the base with an adjustable sliding connection.

11. The device according to claim 1 wherein the pad is rotatably connected to the post assembly to pivot about a horizontal axis.

12. The device according to claim 1 including a tray mountable to the top end of the post assembly.

* * * * *